United States Patent [19]

Kobayashi et al.

[11] Patent Number: 5,585,059

[45] Date of Patent: *Dec. 17, 1996

[54] WATER SOLUBLE ALGIN FIBERS AND PRODUCTION THEREOF

[75] Inventors: Yoshinari Kobayashi, Takamatsu; Hiroshi Kamishima, Ryonancho; Satoshi Fukuoka, Takamatsu; Hideki Obika, Sakaide; Tsutomu Asaoka, Izumiotsu; Keishi Tenma, Sakai, all of Japan

[73] Assignees: Sakai Chemical Industry Co., Ltd.; Agency of Industrial Science and Technology, Japan

[*] Notice: The portion of the term of this patent subsequent to Jan. 22, 2011, has been disclaimed.

[21] Appl. No.: 141,109

[22] Filed: Oct. 26, 1993

Related U.S. Application Data

[63] Continuation of Ser. No. 643,936, Jan. 22, 1991, Pat. No. 5,474,781.

[30] Foreign Application Priority Data

Jan. 23, 1990 [JP] Japan ................................. 2-014534
Dec. 28, 1990 [JP] Japan ................................. 2-409387

[51] Int. Cl.⁶ .................................................... A61K 9/00
[52] U.S. Cl. .................................... 264/186; 536/3
[58] Field of Search .......................... 536/3; 264/176.1, 264/176.11, 203, 178 F, 178 R, 186

[56] References Cited

U.S. PATENT DOCUMENTS

| | | | |
|---|---|---|---|
| 2,600,506 | 6/1952 | Johnson et al. | |
| 3,067,743 | 12/1962 | Merton et al. | 424/431 |
| 3,446,625 | 5/1969 | Blethen | 426/590 |
| 3,762,413 | 10/1973 | Hanke | 604/15 |
| 4,053,627 | 11/1977 | Scher | 424/278 |
| 4,393,048 | 7/1983 | Mason, Jr. et al. | 514/944 |
| 4,543,409 | 9/1985 | Diamantoglou et al. | 536/68 |
| 4,695,463 | 9/1987 | Yang et al. | 514/965 |
| 5,230,853 | 7/1993 | Colegrove et al. | 264/186 |
| 5,264,422 | 11/1993 | della Valle et al. | 514/26 |

FOREIGN PATENT DOCUMENTS

| | | |
|---|---|---|
| 0040048 | 11/1981 | European Pat. Off. . |
| 0072680 | 2/1983 | European Pat. Off. . |

OTHER PUBLICATIONS

McIntyre et al., "Fibers, Manufacture", Encyclopedia of Polymer Science and Engineering, vol. 6, pp. 802–839 1986 (month unavailable), John Wiley & Sons.

"Contemporary Polymer Science", pp. 514–517, Prentice-Hall USA (1981).

Kirk–Othmer, "Encyclopedia of Chemical Technology", Third edition, (1980) 10 pp. 148–155; 12, pp. 45–51.

"Hawley's Condensed Chemical Dictionary" 11th Edition, Van Nostrand Reinhold Company, Inc., pp. 9, 409, 414,419, 424,489,661,769,896,897 (1987).

*Primary Examiner*—Jeffrey C. Mullis
*Attorney, Agent, or Firm*—Wenderoth, Lind & Ponack

[57] ABSTRACT

There is disclosed water soluble algin fibers and such fibers which have antibiotics immobilized thereto. The water soluble algin fibers are produced by extruding an aqueous dope which contains water soluble algin therein into a large quantity of a hydrophilic organic solvent exemplified by acetone. The water soluble algin fibers which have antibiotics immobilized thereto are produced in the same manner by using a dope containing antibiotics.

21 Claims, 2 Drawing Sheets

WATER SOLUBLE ALGIN FIBERS AND
PRODUCTION THEREOF

This is a continuation of Ser. No. 07/643,936 filed Jan. 22, 1991 now U.S. Pat. No. 5,474,781.

FIELD OF THE INVENTION

This invention relates to water soluble algin fibers and such fibers which have antibiotics immobilized thereto, and production thereof.

BACKGROUND OF THE INVENTION

Water insoluble algin fibers have been produced by spinning or extruding water soluble algin solutions into a coagulating bath which is composed of an aqueous solution of multivalent metal ions. When a coagulating bath contains copper or calcium ions, water insoluble copper or calcium algin fibers are obtained, respectively, as disclosed in Japanese Patent Laid-open No. 56-169809, Europian Patent application No. 0 040 048 or U.S. Pat. No. 3,446,625. The alginates have haemostatic properties, and therefore fabrics of such algin fibers are used as swabs or dressings and the like suitable for medical, surgical and other purposes.

There are disclosed in British Patent No. 1,231,506 water solubilized alginate calcium/sodium fibers which are produced by acidifying water insoluble alginate calcium fibers and then treating the acidified fibers with an alcoholic solution of sodium hydroxide. Also in European Patent Application No. 0 040 048, there is disclosed a process for the production of nonwoven fabrics of calcium/sodium alginate fibers by acidifying calcium alginate fibers with acetic acid to displace in part calcium ions with sodium ions and then treating the fibers with an alcoholic solution of sodium acetate.

There is further disclosed in Japanese Patent Publication No. 27720/1989 a process wherein water insoluble alginate calcium is extruded into a coagulating bath together with enzymes or microorganisms to produce water insoluble alginate fibers which have thus the enzymes or microorganisms immobilized thereto useful as a bioreactor.

As above described, water insoluble alginate fibers are already known. It is also known that an alginate powder is obtained by adding hydrophilic organic nonsolvent to an aqueous solution of water soluble algin. However, no process has hitherto been known for the production of substantially Hater soluble algin fibers on account of a high solubility of sodium alginate in water in contrast to calcium alginate which is very slightly soluble in water. More specifically, the extrusion of an aqueous solution of water soluble algin or a dope into a nonsolvent in which water algin is insoluble fails to provide continuous filaments of the water soluble algin in a stable manner because of a high compatibility of the water soluble algin to water.

SUMMARY OF THE INVENTION

The present inventors have made extensive investigations and found that the extrusion of an aqueous spinning solution of water soluble algin or a dope into a coagulating bath of a large quantity of a hydrophilic organic nonsolvent in which the water soluble algin is substantially insoluble and the prompt displacement of the water in the dope with the nonsolvent provides successfully continuous filaments of the water soluble algin.

Therefore, it is an object of the invention to provide water soluble algin fibers, and in particular, such water soluble algin fibers to which antibiotics are immobilized.

It is a further object of the invention to provide method of producing water soluble algin fibers and such fibers which have antibiotics immobilized thereto.

DETAILED DESCRIPTION OF THE INVENTION

Figure 1:
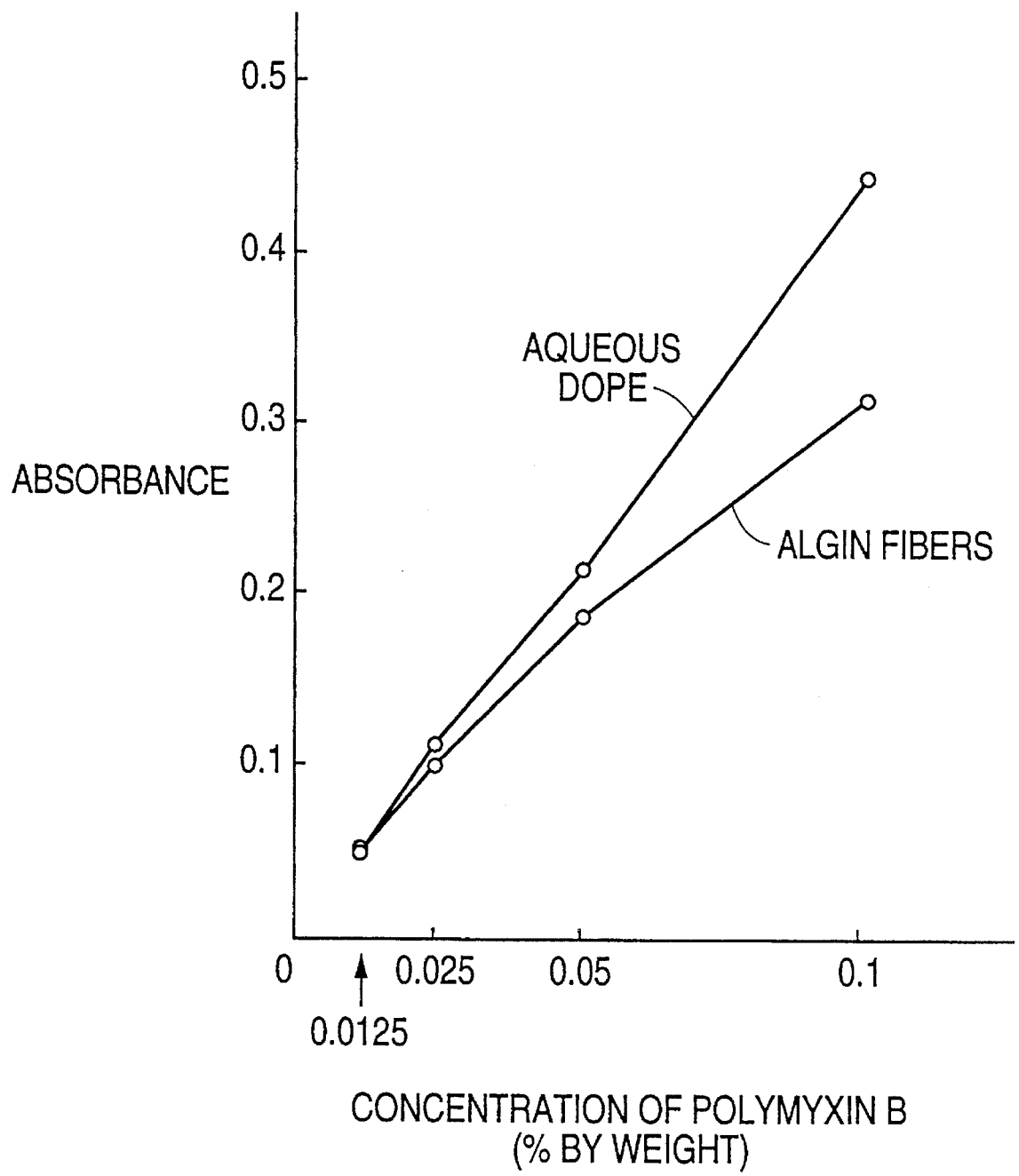
FIG. 1 shows absorbance at 562 nm of a dope containing polymyxin B and water soluble algin fibers produced from the dope and to which polymyxin B is immobilized in relation to the concentration of polymyxin 11 in the dope.

The water soluble algin used in the invention includes, for example, inorganic salts such as sodium, lithium, potassium, magnesium or ammonium salts, organic amine salts such as triethanol amine salt, and organic esters such as propylene glycol alginate. The water soluble algin may contain different types of salt structures in the molecule, and it also may be used singly or as a mixture of two or more of the above.

Among the above water soluble algins, sodium alginate is preferred since it provides fibers of a high mechanical strength. The potassium salt or propylene glycol ester is preferably used together with the sodium alginate.

The water soluble algin fibers are produced in accordance with the invention by extruding an aqueous solution of the water soluble algin or a dope into a coagulating bath composed of hydrophilic organic nonsolvent. The aqueous dope contains the water soluble algin usually in an amount of 3–20% by weight, preferably 5–10% by weight. When the concentration of the water soluble algin in the dope is too small, neither coagulation nor formation of filaments of algin takes place when the dope is extruded into a coagulating bath.

The organic nonsolvent used for the coagulating bath in the invention is a hydrophilic and low molecular weight organic nonsolvent in which the water soluble algin is substantially insoluble or only slightly soluble so that the water in the aqueous dope is promptly displaced with the nonsolvent when the dope is extruded into the coagulating bath and filaments of the water soluble algin is continuously formed. Namely, when the dope is extruded in to the coagulating bath, the water in the dope is promptly diffused into the nonsolvent so that the aqueous dope is promptly dehydrated to form continuous filaments of the water soluble algin.

The use of a hydrophobic solvent causes no dehydration of the dope and fails to provide the continuous filaments of the water soluble algin. The use of a large molecular weight and hence a high viscosity nonsolvent also fails to provide continuous filaments of the water soluble algin since the dope is very slowly or insufficiently dehydrated in such a bath. Further, the use of a hydrophilic nonsolvent having a large number of hydroxyl groups in the molecule is not suitable as a coagulating bath in the invention since such a nonsolvent has naturally a large affinity with the water soluble algin and the dope is not readily dehydrated.

Accordingly, there may be preferably used as the hydrophilic organic nonsolvent, for instance, a lower aliphatic alcohol having 1–3 carbons such as methanol, ethanol or isopropanol, acetone, dioxane, ethylene glycol monomethyl ether, dimethyl sulfoxide, dimethylformamide, dimethylacetamide, acetonitrile, methyl ethyl ketone or phenol. These nonsolvent may be used singly or as a mixture. Among these nonsolvent, methanol, ethanol or acetone is preferred, and acetone is most preferred since it provides water soluble algin fibers of a high mechanical strength. Some of the above nonsolvents such as methyl ethyl ketone, ethylene glycol monomethyl ether or dimethyl sulfoxide is used preferably together with acetone.

The coagulating bath inevitably contains water to an extent since an aqueous dope is extruded thereinto. Therefore, the bath is allowed to contain water to an extent although it is desirable that the bath contains water in an amount as small as possible.

It is of course necessary that the amount of water in the bath is such that the aqueous dope extruded thereinto forms continuous filaments in the bath. The allowed amount of water in the bath depends upon the individual nonsolvent used and other conditions where the dope is extruded thereinto. However, it is usually desirable that the bath contains a solvent in an amount of not less than 50% by weight, preferably not less than 70% by weight, more preferably not less than 80% by weight. It is most preferred, as hereinabove set forth, that the bath contains water in an amount as small as possible. When the bath contains water in too large an amount, it is difficult or impossible to obtain continuous filaments of the water soluble algin.

From the practical standpoint, the coagulating bath is controlled so that it contains water in a substantially constant and small amount of water by connecting the bath to a nonsolvent dehydration equipment or a dehydrated nonsolvent reservoir through a pump and pipe means to supply the bath with the dehydrated solvent continuously. The bath may be further maintained at a temperature usually in the range of normal temperature to about 100° C., although depending upon the nonsolvent used or other extrusion conditions of the dope in to the bath.

It is essential of the method of the invention to extrude an aqueous dope of the water soluble algin into a large quantity of such a hydrophilic organic nonsolvent as set out hereinbefore to displace the water in the dope with the solvent promptly, thereby to obtain continuous filaments of the water soluble algin. Therefore, the diameter of openings of a nozzle from which the dope is extruded into the coagulating bath and the extrusion amount of the dope through the nozzle are also important factors in the method of the invention. It is difficult to specifically determine the nozzle diameter and the extrusion amount since a large number of factors are involved in a complicated manner. However, it is in general preferred that a nozzle opening has a diameter of 0.025–1 mm and an extrusion amount of the dope per nozzle is 0.001–1 ml per minute.

In accordance with the invention, after the water soluble algin fibers are formed in the coagulating bath, the fibers are dehydrated with a dehydrating nonsolvent such as methanol, ethanol or acetone. More specifically, the fibers are immersed in the dehydrating nonsolvent, and then air dried or heated under heating.

The water soluble algin fibers may be formed into nonwoven fabrics, for example, by a dry process such as a carding method.

Further in accordance with the invention, water soluble algin fibers to which antibiotics are immobilized are obtained by preparing an aqueous dope containing water soluble algin and an antibiotic, and then extruding the dope into a coagulating bath composed of the hydrophilic organic solvent as hereinbefore described.

There may be preferably used a hydrophilic and cationic antibiotic since it is immobilized to water soluble algin with a high immobilization rate. From the standpoint of application, antibiotics for external application are preferably used. Such antibiotics include, for example, cephem antibiotics such as ceftizoxime or cefmenoxime, penicillin antibiotics such as benzylpenicillin, sulbenicillin, ampicillin or penicillin G, aminoglycoside antibiotics such as kanamycin, tobramycin, dibekacin, gentamycin, micronomycin, asomycin or fradiomycin, macrolide-lincomycin antibiotics such as erythromycin or kitasamycin, tetracycline antibiotics such as oxytetracycline, tetracycline or demethylchlortetracycline, antibacterial antibiotics such as colistin, polymyxin B, chrolamphenicol, micomycin, bacitracin, gramicidin S or fusidic acid, and anti fungal substances such as amphotericin B, nystatin, trichomycin, pimaricin, variotin, pyrrolnitrin or saccanin. These antibiotics may be used singly or as a mixture. Antibiotics for injection use may also be used.

The reason why the antibiotics are immobilized to water soluble algin has not yet been clarified, but it is likely as one aspect that carboxyl groups of the algin act as a medium for cation exchange, and cation exchange reaction between the antibiotic and the cation of the carboxyl groups such as sodium ion take place to combine or immobilize the antibiotic to the algin.

The water soluble algin fibers which have antibiotics immobilized thereto may also be formed into nonwoven fabrics.

The water soluble algin fibers to which antibiotics are immobilized may also be produced by first forming algin fibers and then immersing the fibers in a solution of antibiotics.

The water soluble algin fibers of the invention may be used as swabs or dressings and the like suitable for medical and surgical purposes. In particular, the fibers which have antibiotics immobilized thereto are antimicrobial, and thus can be used suitably as swabs or dressings to burned or scalded skin for prevention of suppuration, for example, with microbes.

The invention will be described with reference to examples, however, the invention is not limited thereto. In the following examples, a coagulating bath is composed of three liters of a nonsolvent. The fineness and strength of fibers are averages of three times measurements.

EXAMPLE 1

Sodium alginate was added to distilled water and stirred for about 4 hours to prepare a 5% by weight aqueous solution. The solution was filtered through a 200 mesh filter cloth to prepare a dope. The dope was charged in a continuous wet spinning machine and defoamed overnight under reduced pressure.

The dope was extruded at a rate of 12 g per minute into a coagulating bath of varied nonsolvents at 18° C. through a nozzle provided with 1000 openings each having a diameter of 0.1 min. The resultant fibers were rolled at rate of 0.5 m per minute on to a godet roller.

The fibers were immersed in acetone, an excess of the acetone was wiped out, and dried at 100° C. The fineness and strength of the fibers are shown in Table 1.

TABLE 1

| Coagulating Bath | Fineness (denier) | Strength (gf/denier) |
| --- | --- | --- |
| Methanol | 5.463 | 0.236 |
| Ethanol | 4.734 | 0.250 |
| Isopropanol[1] | 4.491 | 0.338 |
| Acetone | 4.410 | 0.312 |

Notes:
55° C.

EXAMPLE 2

The same dope as in the Example 1 was extruded into ethanol at varied temperatures at a rate of 12 g per minute through a nozzle provided with 1000 openings each having a diameter of 0.1 mm. The resultant fibers were dried in the same manner as in the Example 1. The fineness and strength of the fibers are shown in Table 2.

TABLE 2

| Coagulating Bath Temperature (°C.) | Fineness (denier) | Strength (gf/denier) |
| --- | --- | --- |
| 15 | 1.42 | 0.348 |
| 25 | 1.40 | 0.336 |
| 35 | 1.30 | 0.343 |
| 45 | 1.42 | 0.292 |
| 55 | 1.45 | 0.247 |

EXAMPLE 3

The same dope as in the Example 1 was extruded into ethanol at 10° C. at varied rates through a nozzle provided with 1000 openings each having a diameter of 0.1 mm. The resultant fibers were dried in the same manner as in the Example 1. The fineness and strength of the fibers are shown in Table 3.

TABLE 3

| Extrusion Rate (g/min.) | Fineness (denier) | Strength (gf/denier) |
| --- | --- | --- |
| 3.62 | —[1] | —[1] |
| 7.95 | —[1] | —[1] |
| 11.96 | —[2] | —[2] |
| 16.42 | 1.43 | 0.239 |
| 20.77 | 1.81 | 0.300 |

Notes:
[1] No filament was formed.
[2] Strength was too small.

EXAMPLE 4

The same dope as in the Example 1 was extruded into acetone at 10° C. at varied rates through a nozzle provided with 1000 openings each having a diameter of 0.1 The resultant fibers were dried in the same manner as in the Example 1. The fineness and strength of the fibers are shown in Table 4.

TABLE 4

| Extrusion Rate (g/min.) | Fineness (denier) | Strength (gf/denier) |
| --- | --- | --- |
| 3.62 | —[1] | —[1] |
| 7.95 | 0.80 | 0.648 |
| 11.96 | 1.13 | 0.809 |
| 16.42 | 1.49 | 0.649 |
| 20.77 | 1.82 | 0.634 |

Notes:
[1] No filament was formed.

EXAMPLE 5

The same dope as in the Example 1 was extruded into acetone at 10° C. at varied rates through a nozzle provided with 1000 openings each having a diameter of 0.055 mm. The resultant fibers were rolled at a rate of 5.7 m per minute onto a godet roller and dried in the same manner as in the Example 1. The fineness and strength of the fibers are shown in Table 5.

TABLE 5

| Extrusion Rate (g/min.) | Fineness (denier) | Strength (gf/denier) |
| --- | --- | --- |
| 3.62 | 0.40 | 0.812 |
| 7.95 | 0.76 | 0.718 |
| 11.96 | 1.13 | 0.506 |
| 16.42 | 1.45 | 0.511 |
| 20.77 | 2.07 | 0.316 |

EXAMPLE 6

The same dope as in the Example 1 was extruded into acetone at 10° C. at a rate of 12 g per minute through a nozzle provided with openings of varied diameters. The resultant fibers were rolled at a rate of 4.3 m per minute onto a godet roller and dried in the same manner as in the Example 1. The fineness and strength of the fibers are shown in Table 6.

TABLE 6

| Opening Diameter (mm) | Fineness (denier) | Strength (gf/denier) |
| --- | --- | --- |
| 0.055[1] | 2.65 | 0.309 |
| 0.1[1] | 4.08 | 0.368 |
| 0.15[1] | 3.78 | 0.429 |
| 0.2[2] | 16.56 | 0.026 |
| 0.25[3] | 10.97 | 0.026 |

Notes:
[1] Openings: 1000
[2] Openings: 250
[3] Openings: 100

EXAMPLE 7

The same dope as in the Example 1 was extruded into ethanol at 10° C. at a rate of 16 g per minute through a nozzle provided with 1000 openings each having a diameter of 0.1 mm. The resultant fibers were rolled at a rate of 5.7 m per minute onto a godet roller and then dried in the same manner as in the Example 1 with use of varied dehydration solvents. The fineness and strength of the fibers are shown in Table 7.

TABLE 7

| Dehydration Solvent | Fineness (denier) | Strength (gf/denier) |
|---|---|---|
| Methanol | 1.46 | 0.503 |
| Ethanol | 1.51 | 0.336 |
| Acetone | 1.47 | 0.280 |

EXAMPLE 8

The same dope as in the Example 1 was extruded into dimethylacetamide at 15° C. at a rate of 16 g per minute through a nozzle provided with 1000 openings each having a diameter of 0.1 min. The resultant fibers were rolled onto a godet roller and dried in the same manner as in the Example 1.

EXAMPLE 9

The same dope as in the Example 1 was extruded into acetonitrile at 15° C. at a rate of 16 g per minute through a nozzle provided with 1000 openings each having a diameter of 0.1 mm. The resultant fibers were rolled onto a godet roller and dried in the same manner as in the Example 1.

EXAMPLE 10

The same dope as in the Example 1 was extruded into methyl ethyl ketone at 15° C. at a rate of 16 g per minute through a nozzle provided with 1000 openings each having a diameter of 0.1 mm. The resultant fibers were rolled onto a godet roller and dried in the same manner as in the Example 1.

EXAMPLE 11

The same dope as in the Example 1 was extruded into phenol at 15° C. at a rate of 16 g per minute through a nozzle provided with 1000 openings each having a diameter of 0.1 mm. The resultant fibers were rolled onto a godet roller and dried in the same manner as in the Example 1.

EXAMPLE 12

The same dope as in the Example 1 was extruded into acetone at 18° C. at a rate of 16.4 g per minute through a nozzle provided with 1000 openings each having a diameter of 0.055 mm. The resultant fibers were rolled onto a godet roller of a diameter of 11.2 cm at varied rotation rates and dried in the same manner as in the Example 1. The fineness and strength of the fibers are shown in Table 8 in relation to rotation rates of the godet roller.

TABLE 8

| Rotation Rate (rpm) | Fineness (denier) | Strength (gf/denier) |
|---|---|---|
| 2 | —[1] | —[1] |
| 4 | 5.01 | 0.238 |
| 8 | 1.98 | 0.434 |
| 16 | 1.08 | 0.774 |
| 24 | 0.72 | 0.792 |
| 32 | 0.53 | 0.923 |
| 40 | 0.41 | 0.879 |
| 48 | 0.27 | 0.624 |
| 56 | —[1] | —[1] |

Notes:
[1] No filament was formed.

EXAMPLE 13

The same dope as in the Example 1 was extruded into acetone at 13° C. at a rate of 16.4 g per minute through a nozzle provided with 1000 openings each having a diameter of 0.1 mm. The resultant fibers were rolled onto a godet roller of a diameter of 11.2 cm at varied rotation rates and dried in the same manner as in the Example 1. The fineness and strength of the fibers are shown in Table 9.

TABLE 9

| Rotation Rate (rpm) | Fineness (denier) | Strength (gf/denier) |
|---|---|---|
| 2 | —[1] | —[1] |
| 4 | 3.90 | 0.447 |
| 8 | 2.94 | 0.811 |
| 16 | 1.54 | 0.802 |
| 24 | 0.95 | 0.969 |
| 32 | 0.71 | 1.100 |
| 40 | —[1] | —[1] |

Notes:
[1] No filament was formed.

EXAMPLE 14

The same dope as in the Example 1 was extruded into ethanol at 17° C. at a rate of 16.4 g per minute through a nozzle provided with 1000 openings each having a diameter of 0.1 mm. The resultant fibers were rolled onto a godet roller of a diameter of 11.2 cm at varied rotation rates and dried in the same manner as in the Example 1. The fineness and strength of the fibers are shown in Table 10.

TABLE 10

| Rotation Rate (rpm) | Fineness (denier) | Strength (gf/denier) |
|---|---|---|
| 2 | —[1] | —[1] |
| 4 | 3.95 | 0.112 |
| 8 | 2.22 | 0.080 |
| 16 | 1.20 | 0.151 |
| 24 | 0.74 | 0.132 |
| 32 | —[1] | —[1] |

Notes:
[1] No filament was formed.

EXAMPLE 15

The same dope as in the Example 1 was extruded into acetonitrile at 17° C. at a rate of 16.4 g per minute through a nozzle provided with 1000 openings each having a diameter of 0.1 mm. The resultant fibers were rolled onto a godet roller of a diameter of 11.2 cm at varied rotation rates and dried in the same manner as in the Example 1. The fineness and strength of the fibers are shown in Table 11.

TABLE 11

| Rotation Rate (rpm) | Fineness (denier) | Strength (gf/denier) |
|---|---|---|
| 2 | —[1] | —[1] |
| 4 | 4.12 | 0.210 |
| 8 | 2.00 | 0.165 |
| 16 | 1.04 | 0.240 |
| 24 | 0.69 | 0.286 |

TABLE 11-continued

| Rotation Rate (rpm) | Fineness (denier) | Strength (gf/denier) |
| --- | --- | --- |
| 32 | 0.45 | 0.111 |
| 40 | —[1] | —[1] |

Notes:
[1] No filament was formed.

EXAMPLE 16

The same dope as in the Example 1 was extruded into dioxane at 17° C. at a rate of 16.4 g per minute through a nozzle provided with 1000 openings each having a diameter of 0.1 mm. The resultant fibers were rolled on to a godet roller of a diameter of 11.2 cm at varied rotation rates and dried in the same manner as in the Example 1. The fineness and strength of the fibers are shown in Table 12.

TABLE 12

| Rotation Rate (rpm) | Fineness (denier) | Strength (gf/denier) |
| --- | --- | --- |
| 2 | —[1] | —[1] |
| 4 | 4.75 | 0.413 |
| 8 | 2.30 | 0.326 |
| 16 | 1.18 | 0.461 |
| 24 | 0.81 | 0.415 |
| 32 | 0.56 | 0.371 |
| 40 | —[1] | —[1] |

Notes:
[1] No filament was formed.

EXAMPLE 17

The same dope as in the Example 1 was extruded into a mixture of acetone and methyl ethyl ketone at 17° C. at a rate of 16.4 g per minute through a nozzle provided with 1000 openings each having a diameter of 0.1 mm. The resultant fibers were rolled onto a godet roller of a diameter of 11.2 cm at a rotation rate of 16 rpm and dried in the same manner as in the Example 1. The fineness and strength of the fibers in relation to the volume ratio of acetone to methyl ethyl ketone are shown in Table 13.

TABLE 13

| Volume Ratio | Fineness (denier) | Strength (gf/denier) |
| --- | --- | --- |
| 10/0 | 1.16 | 0.821 |
| 9/1 | 1.24 | 0.776 |
| 8/2 | 1.21 | 0.800 |
| 6/4 | 1.23 | 0.746 |
| 4/6 | 1.25 | 0.473 |

EXAMPLE 18

Magnesium alginate was added to distilled water and stirred for about 4 hours to prepare a 5% by weight aqueous solution. The solution was filtered through a 200 mesh filter cloth to prepare a dope. The dope was charged in a continuous wet spinning machine and defoamed overnight under reduced pressure.

The dope was extruded at a rate of 16.4 g per minute into acetone at 17° C. through a nozzle provided with 1000 openings each having a diameter of 0.1 mm. The resultant fibers were rolled at varied rates onto a godet roller of a diameter of 11.2 cm.

The fibers were dried in the same manner as in the Example 1. The fineness and strength of the fibers are shown in Table 14.

TABLE 14

| Rotation Rate (rpm) | Fineness (denier) | Strength (gf/denier) |
| --- | --- | --- |
| 4 | —[1] | —[1] |
| 8 | 2.59 | 0.228 |
| 16 | 1.24 | 0.337 |
| 24 | 0.87 | 0.306 |
| 32 | 0.56 | 0.301 |
| 40 | —[1] | —[1] |

Notes:
[1] No filament was formed.

EXAMPLE 19

Lithium alginate was added to distilled water and stirred for about 4 hours to prepare a 5% by weight aqueous solution. The solution was filtered through a 200 mesh filter cloth to prepare a dope. The dope was charged in a continuous wet spinning machine and defoamed overnight under reduced pressure.

The dope was extruded at a rate of 16.4 g per minute into acetone at 18° C. through a nozzle provided with 1000 openings each having a diameter of 0.1 min. The resultant fibers were rolled at varied rates onto a godet, roller of a diameter of 11.2 cm.

The fibers were dried in the same manner as in the Example 1. The fineness and strength of the fibers are shown in Table 15.

TABLE 15

| Rotation Rate (rpm) | Fineness (denier) | Strength (gf/denier) |
| --- | --- | --- |
| 4 | —[1] | —[1] |
| 8 | 3.41 | 0.265 |
| 16 | 1.61 | 0.157 |
| 24 | 1.09 | 0.278 |
| 32 | —[1] | —[1] |

Notes:
[1] No filament was formed.

EXAMPLE 20

Ammonium alginate was added to distilled water and stirred for about 4 hours to prepare, a 5% by weight aqueous solution. The solution was filtered through a 200 mesh filter cloth to prepare a dope, The dope was charged in a continuous wet spinning machine and defoamed overnight under reduced pressure.

The dope was extruded at a rate of 16.4 g per minute into acetone at 18° C. through a nozzle provided with 1000 openings each having a diameter of 0.1 mm. The resultant fibers were rolled at varied rates onto a godet roller of a diameter of 11.2 cm.

The fibers were dried in the same manner as in the Example 1. The fineness and strength of the fibers are shown in Table 16.

TABLE 16

| Rotation Rate (rpm) | Fineness (denier) | Strength (gf/denier) |
| --- | --- | --- |
| 4 | —[1] | —[1] |
| 8 | 2.57 | 0.273 |
| 16 | 1.29 | 0.327 |
| 24 | 0.85 | 0.302 |
| 32 | —[1] | —[1] |

Notes:
[1] No filament was formed.

EXAMPLE 21

Triethanolamine alginate was added to distilled water and stirred for about 4 hours to prepare a 5% by weight aqueous solution. The solution as filtered through a 200 mesh filter cloth to prepare a dope. The dope was charged in a continuous wet spinning machine and defoamed overnight under reduced pressure.

The dope was extruded at a rate of 16.4 g per minute into acetone at 13° C. through a nozzle provided with 1000 openings each having a diameter of 0.1 mm. The resultant fibers were rolled at varied rates onto a godet roller of a diameter of 11.2 can.

The fibers were dried in the same manner as in the Example 1. The fineness and strength of the fibers are shown in Table 17.

TABLE 17

| Rotation Rate (rpm) | Fineness (denier) | Strength (gf/denier) |
| --- | --- | --- |
| 4 | —[1] | —[1] |
| 8 | 2.91 | 0.299 |
| 16 | 1.55 | 0.207 |
| 24 | 0.86 | 0.235 |
| 32 | 0.70 | 0.256 |
| 40 | —[1] | —[1] |

Notes:
[1] No filament was formed.

EXAMPLE 22

A mixture of sodium alginate and potassium alginate each in the same amount was added to distilled water and stirred for about 4 hours to prepare a 5% by weight aqueous solution. The solution was filtered through a 200 mesh filter cloth to prepare a dope. The dope was charged in a continuous wet spinning machine and defoamed overnight under reduced pressure.

The dope was extruded at a rate of 16.4 g per minute into acetone at 14° C. through a nozzle provided with 1000 openings each having a diameter of 0.1 mm. The resultant fibers were rolled at varied rates on to a godet roller of a diameter of 11.2 cm.

The fibers were dried in the same manner as in the Example 1. The fineness and strength of the fibers are shown in Table 18.

TABLE 18

| Rotation Rate (rpm) | Fineness (denier) | Strength (gf/denier) |
| --- | --- | --- |
| 4 | —[1] | —[1] |
| 8 | 3.02 | 0.299 |
| 16 | 1.27 | 0.365 |
| 24 | 0.99 | 0.387 |
| 32 | 0.79 | 0.404 |
| 40 | —[1] | —[1] |

Notes:
[1] No filament was formed.

EXAMPLE 23

A mixture of 90% by weight of sodium alginate and 10% by weight of propylene glycol alginate was added to distilled water and stirred for about 4 hours to prepare a 5% by weight aqueous solution. The solution was filtered through a 200 mesh filter cloth to prepare a dope. The dope was charged in a continuous wet spinning machine and defoamed overnight under reduced pressure.

The dope was extruded at a rate of 16.4 g per minute into acetone at 13° C. through a nozzle provided with 1000 openings each having a diameter of 0.1 mm. The resultant fibers were rolled at varied rates on to a godet roller of a diameter of 11.2 mm.

The fibers were dried in the same manner as in the Example 1. The fineness and strength of the fibers are shown in Table 19.

TABLE 19

| Rotation Rate (rpm) | Fineness (denier) | Strength (gf/denier) |
| --- | --- | --- |
| 4 | —[1] | —[1] |
| 8 | 2.68 | 0.540 |
| 16 | 1.40 | 0.611 |
| 24 | 0.95 | 0.704 |
| 32 | 0.69 | 0.684 |
| 40 | —[1] | —[1] |

Notes:
[1] No filament was formed.

EXAMPLE 24

An amount of 1214 ml of distilled water was added to 86 g of sodium alginate and the mixture was kneaded with a kneader for about 4 hours to prepare a 6% by weight aqueous solution. An amount of 1.42 g of polymyxin B sulfate as added to 237 ml of distilled water to prepare an aqueous solution of polymyxin B.

An amount of 1183 g of the alginate solution was added to the antibiotic solution, and the mixture was kneaded with a kneader for about 4 hours. The mixture was filtered through a 200 mesh filter cloth to prepare a dope containing 0.1% by weight of polymyxin B and 5% by weight of sodium alginate.

The dope was extruded at a rate of 16.4 g per minute into acetone through a nozzle provided with 1000 openings each having a diameter of 0.1 mm. The resultant fibers were rolled at a rotation rate of 16 rpm onto a godet roller of a diameter of 11.2 cm.

The fibers were dried in the same manner as in the Example 1 to provide water soluble alginate fibers having 0.1% by weight of polymyxin B immobilized thereto.

EXAMPLES 25–27

The 0.1% by weight aqueous solution of polymyxin B as diluted with a 5% by weight aqueous solution of sodium alginate to 0.05% by weight, 0.025% by weight and 0.0125% by weight, respectively. Using these solutions of polymyxin B, there were produced water soluble alginate fibers having polymixin B immobilized thereto.

The dopes and the alginate fibers prepared in the Examples 24–27 were color-developed with a BCA reagent by a protein colorimetric method, made into a 1% by weight solution of sodium alginate, and the absorbance at 562 nm was measured with a spectrophotometer.

As the results are shown in FIG. 1, the alginate fibers from either of the dopes showed a high absorbance, and in addition, as apparent from the comparison of the absorbances of the fibers with those of the dopes, the antibiotic was found to be immobilized at a high rate.

EXAMPLE 28

An aqueous solution of sodium alginate was prepared in the same manner as in the Example 24. An amount of 1.56 g of tetracycline hydrochloride was added to 260 ml of distilled water to prepare an aqueous solution of tetracycline.

The alginate solution was added to the antibiotic solution and kneaded with a kneader for about 4 hours. The mixture was filtered through a 200 mesh filter cloth to prepare a dope containing 0.1% by weight of tetracycline and 5% by weight of sodium alginate.

The dope was treated in the same manner as in the Example 24 to provide water soluble alginate fibers having 0.1% by weight of tetracycline immobilized thereto.

The 0.1% by weight aqueous solution of tetracycline was diluted with a 5% by weight aqueous solution of sodium alginate to 0.05% by weight, 0.025% by weight and 0.0125% by weight, respectively. Using these solutions of tetracycline, there were produced water soluble alginate fibers having tetracycline immobilized thereto.

Figure 2:
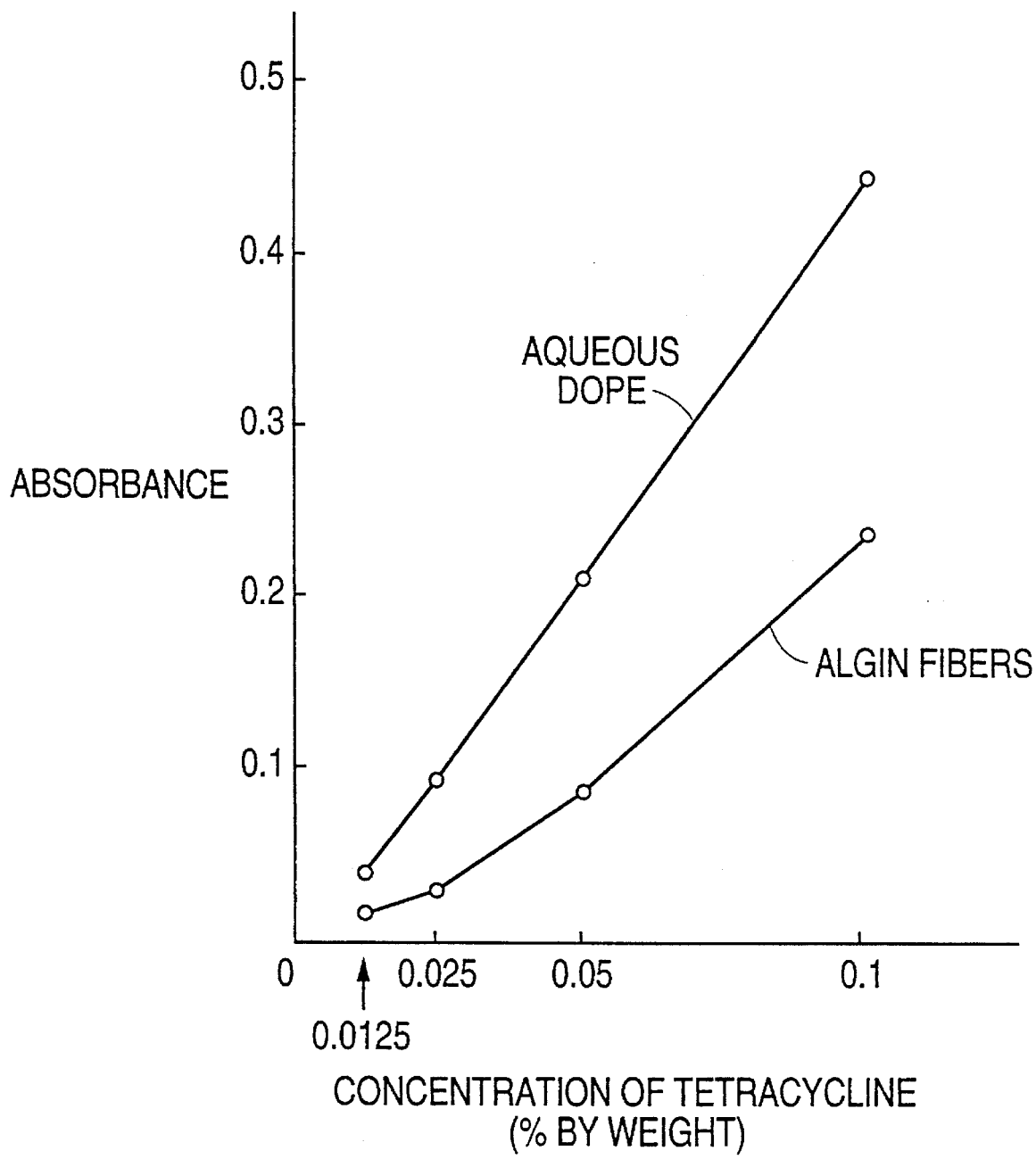
FIG. 2 shows absorbance at 361 nm of a dope containing tetracycline and water soluble algin fibers produced from the dope and to which tetracycline is immobilized in relation to the concentration of tetracycline in the dope.

Making use of the fact that tetracycline has an absorption at 361 nm, the dopes and the fibers prepared in the Examples 28–31 were made into 1% by weight of sodium alginate solutions and the immobilization rate was measured The results are shown in FIG. 2.

Tetracycline was found to be immobilized to the alginate fibers at a somewhat smaller immobilization rate than polymyxin B, however, the immobilization rate was found not less about 65%.

COMPARATIVE EXAMPLE 1

The dope containing 0.1% by weight of polymyxin B as prepared in the Example 24 was extruded into a 5% by weight aqueous solution of calcium chloride, and otherwise in the same manner as in the Example 24, water insoluble algin fibers were prepared. However, the fibers were found to have substantially no polymyxin B immobilized thereto by the same measurement as before mentioned.

COMPARATIVE EXAMPLE 2

The dope containing 0.1% by weight of tetracycline as prepared in the Example 28 was extruded into a 5% by weight aqueous solution of calcium chloride, and otherwise in the same manner as in the Example 28, water insoluble algin fibers were prepared. However, the fibers were found to have substantially no tetracycline immobilized thereto by the same measurement as before mentioned.

EXAMPLE 32

0.05% by weight aqueous solution of amikacin sulfate was used, and otherwise in the same manner as in the Example 24, water soluble algin fibers were prepared which had the antibiotic immobilized thereto.

EXAMPLE 33

A 0.05% by weight aqueous solution of gramicidin S hydrochloride was used, and otherwise in the same manner as in the Example 24, water soluble algin fibers were prepared which had the antibiotic immobilized thereto.

COMPARATIVE EXAMPLE 3

An aqueous solution of sodium alginate was prepared in the same manner as in the Example 24, and using the solution as a dope, there was prepared water soluble algin fibers in the same manner as in the Example 24.

The water soluble and water insoluble algin fibers produced in the Examples 24–33 and the Comparative Examples 1–3 were subjected to antibacterial test to Staphylococcus aureus (IFO 13276), Pseudomonas aeruginosa (IFO 13275) and Escherichia coli. (IFO 3972) all of which were given by Fermentation Institute Foundation.

The microbes were each cultivated on a nutrient agar medium at 37° C. over 24 hours, collected, and then about $1 \times 10^5$ cells each were incubated onto the same medium as above to pepare a plane medium.

Then, the algin fibers were each cut to a size of 3 mm in width (1000 of short fibers) and 10 mm in length as test pieces. The test pieces were each placed on the medium, and the microbes were cultivated at 37° C. for 24 hours. It was observed whether there were formed blocking areas around each of the test pieces. When blocking areas were formed and no growth of microbes was observed there, the fibers were taken antibacterial (positive). The results are shown in Table 20. The antibacterial evaluation was made in four grades based on the short axis of the blocking area formed.

TABLE 20

|  | Staphylococus aureus | Pseudomonas aeruginosa | Escherichia coli. |
| --- | --- | --- | --- |
| Example |  |  |  |
| 24 | − | +++ | ++ |
| 25 | − | ++ | ++ |
| 26 | − | ++ | ++ |
| 27 | − | + | ++ |
| 28 | − | ++ | ++ |
| 29 | − | ++ | ++ |
| 30 | − | ++ | ++ |
| 31 | − | + | ++ |
| 32 | ++ | ++ | ++ |
| 33 | +++ | − | − |
| Comparative |  |  |  |
| 1 | − | ± | ± |
| 2 | − | ± | ± |
| 3 | − | − | − |

+++: not less than 6 mm;
++: not less than 4 mm and less than 6 mm;
+: less than 4 mm; and
−: no blocking area formed.

The algin fibers having polymyxin B immobilized thereto as prepared in the Examples 24–27 and the algin fibers having tetracycline immobilized thereto as prepared in the Examples 28–31 were all active against Pseudomonas aeruginosa and Escherichia coli. The fibers prepared in the Example 32 were active against all the microbes tested.

The fibers prepared in the Examples 24–33 were found not active against one of the microbes tested possibly because the microbe had resistance to the antibiotic.

The fibers prepared in the Comparative Examples 1 and 2 were found active against to an extent, but not to Staphylococus aureus. The fibers prepared in the Comparative Examples 3 were found active against neither of the microbes tested.

What is claimed is:

1. A method of producing a water soluble alginate fiber which comprises extruding an aqueous dope consisting essentially of a water soluble alginate selected from the group consisting of sodium alginate, lithium alginate, potassium alginate, magnesium alginate, ammonium alginate, an organic amine salt and a water soluble alginate ester, from a nozzle having openings of a diameter of 0.025–1 mm, into a coagulating bath consisting essentially of a hydrophilic organic nonsolvent in an amount of not less than 50% by weight and water, to displace the water in the dope with the nonsolvent, while continuously rolling the resultant fiber for recovery thereof, thereby to obtain the water soluble alginate fiber.

2. The method as claimed in claim 1, wherein the organic nonsolvent is a lower aliphatic alcohol of 1–3 carbons.

3. The method as claimed in claim 2, wherein the lower aliphatic alcohol is methanol, ethanol or isopropanol.

4. The method as claimed in claim 1, wherein the organic nonsolvent is acetone.

5. The method as claimed in claim 1, wherein the organic nonsolvent is dioxane.

6. The method as claimed in claim 1, wherein the organic nonsolvent is ethylene glycol monomethyl ether.

7. The method as claimed in claim 1, wherein the organic nonsolvent is dimethyl sulfoxide.

8. The method as claimed in claim 1, wherein the organic nonsolvent is dimethylformamide.

9. The method as claimed in claim 1, wherein the organic nonsolvent is dimethylacetamide.

10. The method as claimed in claim 1, wherein the organic nonsolvent is acetonitrile.

11. The method as claimed in claim 1, wherein the organic nonsolvent is methyl ethyl ketone.

12. The method as claimed in claim 1, wherein the organic nonsolvent is phenol.

13. The method as claimed in claim 1, wherein the water soluble alginate is sodium alginate.

14. The method as claimed in claim 1, wherein the organic amine salt is a triethanolamine salt.

15. The method as claimed in claim 1, wherein the water soluble alginate ester is a propylene glycol alginate.

16. The method as claimed in claim 1, wherein the water soluble alginate is a mixture of sodium alginate and potassium alginate.

17. The method as claimed in claim 1, wherein the water soluble alginate is a mixture of sodium alginate and propylene glycol alginate.

18. The method as claimed in claim 1, wherein the opening has a diameter of 0.025–0.25 mm.

19. The method as claimed in claim 1, wherein the dope contains a water soluble alginate in an amount of 3–20% by weight.

20. The method according to claim 1, wherein the hydrophilic organic nonsolvent is present in an amount of not less than 70% by weight.

21. The method according to claim 1, wherein the hydrophilic organic nonsolvent is present in an amount of not less than 80% by weight.

* * * * *